United States Patent
Aki et al.

(10) Patent No.: US 6,875,440 B2
(45) Date of Patent: Apr. 5, 2005

(54) METHOD FOR CONTROLLING TERMITE

(75) Inventors: Seietsu Aki, Osaka (JP); Hiromi Eguchi, Amagasaki (JP)

(73) Assignee: Sumitomo Chemical Company, Limited, Osaka (JP)

( * ) Notice: Subject to any disclaimer, the term of this patent is extended or adjusted under 35 U.S.C. 154(b) by 64 days.

(21) Appl. No.: 10/372,300

(22) Filed: Feb. 25, 2003

(65) Prior Publication Data
US 2003/0175319 A1 Sep. 18, 2003

(30) Foreign Application Priority Data
Feb. 27, 2002 (JP) ........................................ 2002-051954

(51) Int. Cl.$^7$ ............................................... A01N 25/12

(52) U.S. Cl. ........................ 424/409; 424/405; 424/407; 424/408; 424/84; 424/DIG. 11; 514/350

(58) Field of Search ................................. 424/405, 407, 424/408, 409, 84, DIG. 11; 514/350

(56) References Cited

U.S. PATENT DOCUMENTS

| | | | |
|---|---|---|---|
| 5,573,760 A | * 11/1996 | Thorne et al. | ................. 424/84 |
| 6,022,882 A | 2/2000 | Kim et al. | |
| 6,139,858 A | 10/2000 | Fujitomo | |

* cited by examiner

*Primary Examiner*—Neil S. Levy
(74) *Attorney, Agent, or Firm*—Sughrue Mion, PLLC

(57) ABSTRACT

Termites can be controlled by applying an effective amount of N-[2-chloro-3,5-bis(trifluoromethyl)phenyl]-N'-(2,6-difluorobenzoyl)urea supported on cellulose.

7 Claims, No Drawings under reduced pressure to give a solid formulation of the present invention.

METHOD FOR CONTROLLING TERMITE

FIELD OF THE INVENTION

The present invention relates to a method for controlling termite.

BACKGROUND OF THE INVENTION

U.S. Pat. No. 6,022,882 discloses 2-chloro-3,5-bis(trifluoromethyl)phenyl benzoylurea derivatives exhibit growth-retarding activity against insects.

The object of the present invention is to provide a new use of N-[2-chloro-3,5-bis(trifluoromethyl)phenyl]-N'-(2,6-difluorobenzoyl)urea (hereinafter, referred to as bistrifluron) for controlling termite.

SUMMARY OF THE INVENTION

The present invention provides a method for controlling termite which comprises applying an effective amount of bistrifluron supported on cellulose. Further, the present invention also provides a termite-controlling agent which can be a sheet formulation or a solid formulation.

DETAILED DESCRIPTION OF THE INVENTION

Bistrifluron used in the present method is a known compound having insect growth regulating activity and can be produced by the method given in U.S. Pat. No. 6,022,882.

In the present method, bistrifluron supported on cellulose is generally applied to termite tunnel, lumber damaged by termites or a locus termites inhabit. Bistrifluron is usually formulated to a sheet formulation or a solid formulation for application to control termites.

The sheet formulation contains bistrifluron at 0.1 mg to 100 g per 1 $m^2$ in general. The sheet material should be cellulose. Examples of the sheet material include filter paper, recycled paper and unbleached paper. The sheet formulation can be produced by making a bistrifluron solution impregnated with the sheet material and drying. The bistrifluron solution may be prepared by dissolving bistrifluron with an organic solvent such as acetone, methanol, ethanol, isopropyl alcohol and so on.

The solid formulation contains 0.1 to 50% by weight of bistrifluron and 50 to 99.9% by weight supported on wood chips or wood powders in general. Examples of the wood include Japanese red pine, Japanese black pine, larch and Radiata pine, The solid formulation can be produced by adding a bistrifluron solution to wood chips or powders and drying. The bistrifluron solution may be prepared by dissolving bistrifluron with an organic solvent such as acetone, methanol, ethanol, isopropyl alcohol and so on. The solid formulation can also be a mixture of 0.1 to 50% by weight of bistrifluron and cellulose powder, which can be produced by mixing bistrifluron or its solution with cellulose powder, and optionally drying. The cellulose powder may be obtained by pulverizing after acidic hydrolysis of lumber cellulose. The solid formulation including cellulose powder can further contain the other solid carrier, which is exemplified by inorganic powders such as synthetic hydrated silica, anhydrous silica, aluminum oxide, kaolin, talc, titanium oxide and magnesium carbonate; synthetic resin powders such as polyurethane, polyamide and polypropylene; and salts such as calcium stearate. The contents of cellulose and the other solid carrier are generally 50 to 99.9% by weight and 0 to 50% by weight in the solid formulation respectively.

The sheet formulation and the solid formulation can further contain a termite-attractant such as pheromone, glycol ethers and so on. The contents of a termite-attractant is generally 0.01 to 10% by weight in the sheet or solid formulation.

The sheet formulation and the solid formulation can be applied to termite tunnel, lumber damaged by termites or a locus termites inhabit, as they are, but it is preferable to apply a container (bait station) including the sheet formulation or the solid formulation to termite tunnel, lumber damaged by termites or a locus termites inhabit.

Examples of the termites effectively controlled by the present invention include Mastotermitidae such as *Mastotermes* spp.; Termopsidae such as *Zootermopsis* spp., *Archotermopsis* spp., *Hodotermopsis* spp., *Porotermes* spp. and *Stolotermes* spp.; Kalotermitidae such as *Kalotermes* spp., *Neotermes* spp., *Cryptotermes* spp., *Incisitermes* spp. and *Glyptotermes* spp.; Hodotermitidae such as *Hodotermes* spp., *Microhodotermes* spp. and *Anacanthotermes* spp.; Rhinotermitidae such as *Reticulitermes* spp., *Heterotermes* spp., *Coptotermes* spp. and *Schedolinotermes* spp.; Serritermitidae; and Termitidae such as *Amitermes* spp., *Drepanotermes* spp., *Hopitalitermes* spp., *Trinervitermes* spp., *Macrotermes* spp., *Odontotermes* spp., *Microtermes* spp., *Nasutitermes* spp., *Pericapritermes* spp. and *Anoplotermes* spp.

Typical examples of the termites species objected in the present invention include *Mastotermes darwiniensis, Zootermopsis nevadensis, Hodotermopsis japonica, Neotermes koshunensis, Cryptotermes domesticus, Incisitermes minor, Glyptotermes satsumensis, Glyptotermes nakajimai, Glyptotermes fuscus, Glyptotermes kodamai, Glyptotermes kushimensis, Recticulitermes speratus, Reticulitermes miyatakei, Reticulitermes hesperus, Reticulitermes virginicus, Reticulitermes tibialis, Reticulitermes flavipes, Reticulitermes flavipes amamianus, Reticulitermes* sp. (*Kanmonshiroari*), *Heterotermes aureus, Coptotermes formosanus, Coptotermes guangzhoensis, Odontotermes formosanus, Nasutitermnes takasagoensis, Pericapritermes nitobei* and *Sinocapritermes mushae*.

The application dosage of bistrifluron depends on a degree of damage and the other conditions. In case that the present termite-controlling agents are applied to lumber damaged by termites or a locus termites inhabit, the dosage of bistrifluron is usually 0.001 g to 10 g, preferably 0.001 g to 1 g per 1 $m^2$. Further, in case that the present termite-controlling agents are applied to a termite tunnel, the dosage of bistrifluron is usually 0.001 to 1 g, preferably 0.001 to 0.1 g.

EXAMPLES

The present invention is explained by formulation examples and test examples in detail below.

Formulation Example 1

Three-tenth (0.3) part by weight of bistrifluron is added to 99.7 parts of cellulose paper (unbleached paper) and dried overnight at room temperature to give a sheet formulation of the present invention.

Formulation Example 2

A half (0.5) part by weight of bistrifluron is added to 99.5 parts of cellulose paper (unbleached paper) and dried overnight at room temperature to give a sheet formulation of the present invention.

Formulation Example 3

Three-tenth (0.3) part by weight of bistrifluron is added to 99.7 parts of wood chips (Japanese red pine) and dried overnight at room temperature to give a solid formulation of the present invention.

Formulation Example 4

A half (0.5) part by weight of bistrifluron is added to 99.5 parts of wood chips (Japanese red pine) and dried overnight at room temperature to give a solid formulation of the present invention.

Formulation Example 5

A half (0.5) part by weight of bistrifluron is added to 99.5 parts of cellulose powder and dried overnight at room temperature to give a solid formulation of the present invention.

Next, test examples are shown below.

Test Example 1

The sheet formulation obtained in Formulation example 1 or 2 (2.5 g) was put in a plastic cup (8.5 cm in diameter). The plastic cup was set inside a large cup having wet cotton for supplying moisture and 100 Formosan subterranean termites (*Coptotermes formosanus*) were released in the plastic cup. After 2, 4 and 8 weeks, the mortality of the termites was observed. Further, the same sheet formulation as Formulation example 2 except that hexaflumuron was used in place of bistrifluron was tested for reference. The results are given below.

TABLE 1

|  | Mortality (%) | | |
| --- | --- | --- | --- |
|  | 2 weeks | 4 weeks | 8 weeks |
| Formulation example 1 | 16 | 100 | 100 |
| Formulation example 2 | 11 | 100 | 100 |
| Hexaflumuron | 5 | 34 | 100 |
| No treatment | 6 | 10 | 23 |

Hexaflumuron, whose chemical name is 1-[3,5-dichloro-4-(1,1,2,2-tetrafluoroethoxy)phenyl]-3-(2,6-difluorobenzoyl)urea, is also a benzoylurea derivative and it is known as an active ingredient of a termite-controlling agent. As given in the above test results, bistrifluron has more rapid efficacy than hexaflumuron.

The rapid efficacy of bistrifluron is also proved in a field test as followings:

Test Example 2

In a place termites inhabit, two tree stumps (A and B) damaged by Formosan subterranean termites were found. The distance between A and B is about 500 m. Two wooden blocks (ϕ75 mm×78 mm) were buried near A and B, respectively.

After all the wooden blocks were damaged by the termites, each of about 60 g of the sheet formulation obtained in Formulation example 2 was buried in place of the damaged wooden blocks at A. On the other hand, the same sheet formulation as Formulation example 2 except that hexaflumuron was used in place of bistrifluron was used at B. Further, two of the sheet formulation were added at A and B respectively, after two weeks. After that, the state of the termites were observed at each two weeks. The results are given below.

TABLE 2

| After application | Bistrifluron 0.5% | Hexaflumuron 0.5% |
| --- | --- | --- |
| 2 weeks | Bistrifluron was further applied. | Hexaflumuron was further applied. |
| 4 weeks | Workers were not observed. Some soldiers were dead. | Workers and soldiers were observed. |
| 6 weeks | Many soldiers were observed to be dead. | Workers were not observed. Many living soldiers were observed. |
| 8 weeks |  | Many soldiers were observed to be dead. |

Soldiers are usually in their colony. At emergency, soldiers are observed. It is assumed that the colony was fallen by observing many soldiers were dead.

As given in the above test results, bistrifluron also has more rapid efficacy than hexaflumuron in a field test.

What is claimed is:

1. A method for controlling termite which comprises applying an effective amount for controlling termites of N-[2-chloro-3,5-bis(trifluoromethyl)phenyl]-N'-(2,6-difluorobenzoyl)urea supported on cellulose to termite tunnel, lumber damaged by termites or a locus termites inhabit.

2. A method for controlling termites according to claim 1, which comprises applying 0.01 g to 100 g per 1 m$^2$ of N-[2-chloro-3,5-bis(trifluoromethyl)phenyl]-N'-(2,6-difluorobenzoyl)urea to lumber damaged by termites or a locus termites inhabit.

3. A method for controlling termites according to claim 1, which comprises applying 0.01 to 1000 g of N-[2-chloro-3,5-bis(trifluoromethyl)phenyl]-N'-(2,6-difluorobenzoyl) urea to a termite tunnel.

4. A termite-controlling agent which comprises N-[2-chloro-3,5-bis(trifluoromethyl)phenyl]-N'-(2,6-difluorobenzoyl)urea as an active ingredient supported on a cellulose sheet.

5. A termite-controlling agent according to claim 4, which comprises 0.1 mg to 100 g of N-[2-chloro-3,5-bis(trifluoromethyl)phenyl]-N'-(2,6- difluorobenzoyl)urea per 1 m$^2$ of cellulose paper.

6. A termite-controlling agent which comprises N-[2-chloro-3,5-bis(trifluoromethyl)phenyl]-N'-(2,6-difluorobenzoyl)urea as an active ingredient supported on wood chips or wood powder.

7. A termite-controlling agent which comprises N-[2-chloro-3,5-bis(trifluoromethyl)phenyl]-N'-(2,6-difluorobenzoyl)urea as an active ingredient and cellulose powder.

* * * * *